United States Patent
Gudas et al.

(10) Patent No.: US 6,472,000 B1
(45) Date of Patent: Oct. 29, 2002

(54) METHOD OF CONTROLLING RELEASE OF BITTERNESS INHIBITORS IN CHEWING GUM AND GUM PRODUCED THEREBY

(75) Inventors: Victor V. Gudas, Oak Lawn, IL (US); Michael A. Reed, Merrillville, IN (US); Philip G. Schnell, Downers Grove, IL (US); Henry T. Tyrpin, Palos Park, IL (US); David L. Witkewitz, Bridgeview, IL (US); Michael J. Greenberg, Northbrook, IL (US); Fred R. Wolf, West Des Moines, IA (US)

(73) Assignee: WM. Wrigley Jr. Co., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 14 days.

This patent is subject to a terminal disclaimer.

(21) Appl. No.: 09/319,054

(22) PCT Filed: Dec. 23, 1996

(86) PCT No.: PCT/US96/20252

§ 371 (c)(1),
(2), (4) Date: May 26, 1999

(87) PCT Pub. No.: WO98/23166

PCT Pub. Date: Jun. 4, 1998

(51) Int. Cl.⁷ .............................. A23G 3/30; A61K 9/68
(52) U.S. Cl. .............................. 426/3; 424/48; 424/440; 426/5
(58) Field of Search ................ 426/3, 5, 6; 424/48, 424/440

(56) References Cited

U.S. PATENT DOCUMENTS

| | | |
|---|---|---|
| 3,647,483 A | 3/1972 | Eisenstadt |
| 3,684,529 A | 8/1972 | Liggett et al. |
| 3,699,132 A | 10/1972 | Acton et al. |
| 3,753,726 A | 8/1973 | Clinton et al. |
| 3,773,526 A | 11/1973 | Bliznak |
| 4,001,453 A | 1/1977 | Huber et al. ................ 426/533 |
| 4,031,265 A | 6/1977 | Guadagni et al. ........... 426/599 |
| 4,045,581 A | 8/1977 | Mackay et al. .............. 426/3 |
| 4,064,274 A | 12/1977 | Mackay et al. .............. 426/3 |
| 4,154,862 A | 5/1979 | Guadagni et al. ........... 426/536 |
| 4,183,965 A | 1/1980 | Mookherjee et al. ....... 426/548 |
| 4,263,327 A | 4/1981 | Pedersen et al. ............ 426/3 |
| 4,597,972 A | 7/1986 | Taylor ......................... 426/36 |
| 4,822,597 A | 4/1989 | Faust et al. ................. 424/48 |
| 4,832,962 A | 5/1989 | Oppenheimer et al. .... 426/3 |
| 4,978,537 A | 12/1990 | Song ............................ 426/5 |
| 4,988,532 A | 1/1991 | Buckholz, Jr. et al. ..... 426/594 |
| 4,994,490 A | 2/1991 | Roy et al. ................... 514/522 |
| 4,997,659 A | 3/1991 | Yatka et al. ................. 426/3 |
| 5,009,893 A | 4/1991 | Cherukuri et al. .......... 424/440 |
| 5,013,716 A | 5/1991 | Cherukuri et al. .......... 514/23 |
| 5,082,653 A | 1/1992 | Pan et al. .................... 424/54 |
| 5,139,794 A | 8/1992 | Patel et al. .................. 426/3 |
| 5,154,939 A | 10/1992 | Broderick et al. .......... 426/5 |
| 5,192,563 A | 3/1993 | Patel et al. .................. 426/5 |
| 5,232,735 A | 8/1993 | Kurtz et al. ................. 426/649 |
| 5,336,513 A | 8/1994 | Riemer ....................... 426/548 |
| 5,368,845 A | 11/1994 | Gaffar et al. ................ 424/54 |
| 5,372,824 A | 12/1994 | Record et al. ............... 426/3 |
| 5,523,105 A | 6/1996 | Ishikawa et al. ............ 426/538 |

FOREIGN PATENT DOCUMENTS

| | | |
|---|---|---|
| EP | 0 727 149 A2 | 8/1996 |
| JP | 1991-251533 | 11/1991 |
| WO | WO 97/20473 | 6/1997 |
| WO | WO 98/23165 | 6/1998 |
| WO | WO 98/23166 | 6/1998 |
| WO | WO 98/23167 | 6/1998 |

OTHER PUBLICATIONS

Breslin, P.A.S. et al., "Suppression of Bitterness by Sodium: Variation Among Bitter Taste Stimuli," Jun. 1995 (15 pages).

Roy, G., "The Applications and Future Implications of Bitterness Reduction And Inhibition in Food Products," Food Science and Nutrition, 1990, vol. 29, Issue 2, pp. 59–71.

Roy, G., "Bitterness: reduction and inhibition," Trends in Food Science & Technology, Apr. 1992, vol. 3, pp. 85–91.

*Primary Examiner*—Arthur L. Corbin
(74) *Attorney, Agent, or Firm*—Steven P. Shurtz; Brinks Hofer Gilson & Lione

(57) ABSTRACT

A method for producing a chewing gum with a controlled release of a bitterness inhibitor, as well as the chewing gum so produced, is obtained by physically modifying the release properties of the bitterness inhibitor by coating and drying. The bitterness inhibitor is coated by encapsulation, partially coated by agglomeration, entrapped by absorption, or treated by multiple steps of encapsulation, agglomeration, and absorption. The coated bitterness inhibitor is preferably then co-dried and particle sized to produce a release-modified bitterness inhibitor for use in chewing gum. When incorporated into the chewing gum, these particles are adapted to produce a fast release or a delayed release when the gum is chewed. The preferred bitterness inhibitor is sodium gluconate.

31 Claims, No Drawings

METHOD OF CONTROLLING RELEASE OF BITTERNESS INHIBITORS IN CHEWING GUM AND GUM PRODUCED THEREBY

BACKGROUND OF THE INVENTION

The present invention relates to methods for producing chewing gum. More particularly the invention relates to producing chewing gum containing an amount of bitterness inhibitor. The bitterness inhibitor that is added to the chewing gum is treated to control its rate of release in the chewing gum.

In recent years, efforts have been devoted to controlling release characteristics of various ingredients in chewing gum. Most notably, attempts have been made to delay the release of sweeteners and flavors in various chewing gum formulations to thereby lengthen the satisfactory chewing time of the gum. Delaying the release of sweeteners and flavors can also avoid an undesirable overpowering burst of sweetness or flavor during the initial chewing period. On the other hand, some ingredients have been treated so as to increase their rate of release in chewing gum.

Besides sweeteners, other ingredients may require a controlled release from chewing gum. Bitterness inhibitors may be added to gum; however, bitterness inhibitors may vary in their release rate. Some that are not water soluble may be encapsulated in a water soluble matrix such that, during the chewing period, they may be released quickly. This would allow chewing gum to be a carrier for bitter stimulants or medicaments, with the fast release of inhibitors improving the overall quality of the gum.

On the other hand, serious taste problems may arise because of the bitter nature of bitter stimulants and/or medicaments, and a slow release may be desired. Some water soluble bitterness inhibitors may release quickly and not be effective unless their release is modified to a prolonged or delayed release. Thus these inhibitors could be used with slow release stimulants and medicaments to give chewing gum a quality taste. To be most effective, bitterness inhibitors should release from chewing gum at the same time as the bitter causing agent.

Thus there are specific advantages to adding bitterness inhibitor to chewing gum by a controlled release mechanism.

Early high intensity sweeteners had a bitter aftertaste that was modified by using glucono delta lactone, sodium gluconate and/or potassium gluconate, as disclosed in U.S. Pat. Nos. 3,647,483 and 3,684,529. Calcium chloride also reduced the bitterness of saccharin as disclosed in U.S. Pat. No. 3,773,526.

Often bitter medicaments are added to chewing gum and high intensity sweeteners are added to reduce the impression of bitterness, as disclosed in U.S. Pat. No. 4,822,597. A method of reducing bitterness of caffeine in gum is disclosed in Japanese Patent Publication No. 91-251533.

A bitterness inhibitor called neodiosmin is used to reduce bitterness in citrus juices as disclosed in U.S. Pat. No. 4,031,265 and in other foods and artificial sweeteners as disclosed in U.S. Pat. No. 4,154,862.

Other bitterness inhibitors include cyclotetradecenones, disclosed in U.S. Pat. No. 4,183,965; sclareolide, disclosed in U.S. Pat. No. 4,988,532; natural soy flavor, disclosed in U.S. Pat. No. 4,832,962; N-sulfomethyl-N-arylureas disclosed in U.S. Pat. No. 4,994,490; sodium, potassium and ammonium salts of ferulic acid and caffeic acid, disclosed in U.S. Pat. No. 5,336,513; and numerous compounds, including 2,4-dihydroxy benzoic acid, disclosed in U.S. Pat. No. 5,232,735.

Other patents disclose that menthol bitterness may be reduced by using artificial cooling agents such as those found in U.S. Pat. No. 5,009,893. Mint flavor may be modified as in U.S. Pat. No. 5,372,824 by removing a part of the 1-menthol, or as in U.S. Pat. No. 5,523,105 by adding polygodial plant extracts. Late chew bitterness in high mint-flavor content gums may be reduced by adding a granulated cellulose/Zein mixture, as disclosed in U.S. Pat. No. 5,192,563.

U.S. Pat. No. 5,139,794 discloses encapsulated sodium chloride to enhance flavor and sweetness in chewing gum. U.S. Pat. No. 5,154,939 also discloses the use in chewing gum of sodium chloride in an encapsulation matrix.

SUMMARY OF THE INVENTION

The present invention is a method of producing chewing gum with bitterness inhibitors which have been physically modified to control their release. The present invention also relates to the chewing gum so produced. These inhibitors may be added to sucrose type gum formulations, replacing a small quantity of sucrose. The formulation may be a low or high moisture formulation containing low or high amounts of moisture containing syrup. These inhibitors may also be used in low or non-sugar gum formulations, replacing a small quantity of sorbitol, mannitol, other polyols or carbohydrates. Non-sugar formulations may include low or high moisture sugar free chewing gums.

Bitterness inhibitors may be combined or co-dried with bulk sweeteners typically used in chewing gum, such as sucrose, dextrose, fructose and maltodextrins, as well as sugar alcohols such as sorbitol, mannitol, xylitol, maltitol, lactitol, hydrogenated isomaltulose and hydrogenated starch hydrolyzates.

The modified release rate noted above may be a fast release or a delayed release. The modified release of bitterness inhibitors is obtained by encapsulation, partial encapsulation or partial coating, entrapment or absorption with high or low water soluble materials or water insoluble materials. The procedures for modifying the bitterness inhibitors include spray drying, spray chilling, fluid bed coating, coacervation, extrusion and other agglomerating and standard encapsulating techniques. Bitterness inhibitors may also be absorbed onto an inert or water-insoluble material. Bitterness inhibitors may be modified in a multiple step process comprising any of the processes, or a combination of the processes noted. Prior to encapsulation, bitterness inhibitors may also be combined with bulk sweeteners including sucrose, dextrose, fructose, maltodextrin or other bulk sweeteners, as well as sugar alcohols such as sorbitol, mannitol, xylitol, maltitol, lactitol, hydrogenated isomaltulose and hydrogenated starch hydrolyzates.

Prior to encapsulation, bitterness inhibitors may be combined with high-intensity sweeteners, including but not limited to thaumatin, aspartame, alitame, acesulfame K, saccharin acid and its salts, glycyrrhizin, cyclamate and its salts, stevioside and dihydrochalcones. Co-encapsulation of bitterness inhibitors along with a high-intensity sweetener may reduce the bitterness of stimulants and/or medicaments and control the sweetener release with the inhibitor. This can improve the quality of the gum product and increase consumer acceptability.

Preferable bitterness inhibitors include ferulic acid, sodium gluconate, sodium ascorbate, sodium ferulate, sodium acetate, sodium glycinate and calcium glycerolphosphate. These bitterness inhibitors may be combined with stimulants and/or medicaments prior to encapsulation to reduce the overall bitterness caused by stimulants and/or medicaments and result in a gum product having increased consumer acceptability.

DETAILED DESCRIPTION OF THE PREFERRED EMBODIMENTS

Caffeine is a natural chemical found in a variety of food products such as coffee, tea, cocoa, chocolate, and various other beverages. Caffeine is known as an effective stimulant to increase energy and reduce drowsiness. However, caffeine has a naturally bitter taste that significantly reduces the taste quality of chewing gum in which it is used.

When caffeine is added to chewing gum at a level of about 0.2% to about 5%, caffeine imparts an intense bitterness to the chewing gum that lasts throughout the chewing period. The higher the level used, the stronger the bitterness. Taste limits in chewing gum are generally about 0.4% (10 mg) to about 4% (100 mg) of caffeine in a stick of gum. The 60–80 mg level of caffeine is about the level of caffeine found in a conventional cup of coffee. The target level of caffeine in stick gum is about 40 mg per stick, with a range of about 25–60 mg, so that a five stick package of gum would contain about 200 mg of caffeine, or the equivalent of caffeine in two strong cups of coffee. However, at this level caffeine bitterness overwhelms the flavor initially and lasts throughout the chewing period.

If the caffeine was modified to give a fast release in chewing gum, this would also result in a fast release of bitterness. To some degree sugars and/or high intensity sweeteners may mask this bitterness, but something to inhibit the bitterness without adding other tastes is preferred.

As discussed previously, there are a wide variety of bitterness inhibitors used in food products. Some of the preferred bitterness inhibitors are the sodium salts as discussed in the article *Suppression of Bitterness by Sodium: Variations Among Bitter Taste Stimuli*, by P. A. S. Breslin and G. K. Beauchamp from Monell Chemical Senses Center, Philadelphia, Pa. Sodium salts discussed are sodium acetate and sodium gluconate. Other sodium salts that may also be effective are sodium glycinate, sodium ascorbate and sodium glycerolphosphate. Among these, the most preferred is sodium gluconate, since it has a low salty taste and is most effective to reduce bitterness of caffeine and urea.

Most of the sodium salts are very water soluble and are readily released from chewing gum to function as bitterness inhibitors. Some solubilities are:

sodium gluconate-69% at 25° C.
sodium ascorbate-62% at 25° C.
sodium acetate-56% at 25° C.
sodium glycerolphosphate-40% at 25° C.

In some instances, the sodium salts which release readily from chewing gum may be modified by encapsulation to give an even faster release from chewing gum. However, in most instances the sodium salts would be encapsulated or entrapped to give a delayed release from gum.

Not only would a delayed release of a bitterness inhibitor be effective for caffeine but also when used with high menthol type gum flavors. Menthol is a common ingredient in peppermint flavor that causes a bitterness in gum in the later stages of chewing. A delayed release bitterness inhibitor can reduce this flavor bitterness in the later stages.

Other bitterness inhibitors that are not very water soluble may release slowly and may not be effective bitterness reducers with some stimulants and/or medicaments. As a result, encapsulation for fast release may be desired for these bitterness inhibitors. Other inhibitors may have a moderate release and these may be entrapped to give a much longer delayed release.

The release rate of a bitterness inhibitor should be designed to release with the ingredient for which it is masking bitterness, whether it be a flavor, a stimulant like caffeine, or a medicament. In some instances, a bitterness inhibitor may be co-encapsulated with the bitter causing agent to release together during the chewing period. If desired, high intensity sweeteners may be added to this mixture to further reduce bitterness and obtain an acceptable product.

Levels of bitterness inhibitors will vary according to the intensity of the bitter agent and the intensity of the bitterness inhibitor. Generally, bitterness inhibitors will be about 0.01% to about 8% and preferably about 0.05% to about 4%. For gum products that may have menthol as the bitter agent from a flavor, low levels of about 0.05% to about 1% may be satisfactory. For gum products that may contain caffeine or other bitter stimulants, these levels may be about 0.5% to about 4%. Of course, some bitterness inhibitors may be unacceptable at high levels. However, sodium gluconate has a bland taste and may be used at levels as high as 4%. Therefore, sodium gluconate is the preferred bitterness inhibitor for chewing gum.

Bitterness inhibitors can be added to chewing gum as a powder, as an aqueous dispersion, or dispersed in glycerin, propylene glycol, corn syrup, hydrogenated starch hydrolyzate, or any other compatible aqueous dispersion.

For aqueous dispersions, an emulsifier can also be mixed in the solution with the bitterness inhibitors and the mixture added to a chewing gum. A flavor can also be added to the bitterness inhibitors/emulsifier mixture. The emulsion formed can be added to chewing gum. Bitterness inhibitors in powder form may also be mixed into a molten chewing gum base during base manufacture or prior to manufacture of the gum. Bitterness inhibitors may also be mixed with base ingredients during base manufacture.

As stated previously, bitterness inhibitors release at various rates from chewing gum during the early stages of mastication of the gum because of their varying solubility in water. Physical modifications of the bitterness inhibitor by encapsulation with highly water soluble substrates will increase their release in chewing gum by increasing the solubility or dissolution rate. Any standard technique which gives partial or full encapsulation can be used. These techniques include, but are not limited to, spray drying, spray chilling, fluid-bed coating and coacervation. These encapsulation techniques may be used individually in a single step process or in any combination in a multiple step process. The preferred technique for fast release of bitterness inhibitors is spray drying.

Bitterness inhibitors may also be encapsulated or entrapped to give a delayed release from chewing gum. A slow, even release can give a reduced bitterness over a long period of time and blend more easily with longer lasting flavors and sweeteners. Bitterness inhibitors may be encapsulated with sweeteners, specifically high-intensity sweeteners such as thaumatin, dihydrochalcones, acesulfame K, aspartame, sucralose, alitame, saccharin and cyclamates.

The encapsulation techniques described herein are standard coating techniques and generally give varying degrees of coating from partial to full coating, depending on the coating composition used in the process. Generally, compositions that have high organic solubility, good film-forming properties and low water solubility give better delayed release, while compositions that have high water solubility give better fast release. Such low water-solubility compositions include acrylic polymers and copolymers, carboxyvinyl polymer, polyamides, polystyrene, polyvinyl acetate, polyvinyl acetate phthalate, polyvinylpyrrolidone and waxes. Although all of these materials are possible for encapsulation of bitterness inhibitors, only food-grade materials should be considered. Two standard food-grade coating materials that are good film formers but not water soluble are shellac and Zein. Others which are more water soluble, but good film formers, are materials like agar, alginates, a wide range of cellulose derivatives like ethyl cellulose, methyl cellulose, sodium hydroxymethyl cellulose, and hydroxypropylmethyl cellulose, dextrin, gelatin, and modified starches. These ingredients, which are generally approved for food use, may give a fast release when used as an encapsulant for bitterness inhibitors. Other encapsulants like acacia or maltodextrin can also encapsulate bitterness inhibitors and give a fast release rate from gum.

The amount of coating or encapsulating material on the bitterness inhibitors may also control the length of time for its release from chewing gum. Generally, the higher the level of coating and the lower the amount of active bitterness inhibitors, the slower the release during mastication with low water soluble compositions. The release rate is generally not instantaneous, but gradual over an extended period of time. To obtain the delayed release to blend with a gum's flavor release, the encapsulant should be a minimum of about 20% of the coated bitterness inhibitors. Preferably, the encapsulant should be a minimum of about 30% of the coated bitterness inhibitors, and most preferably should be a minimum of about 40% of the coated bitterness inhibitors. Depending on the coating material, a higher or lower amount of coating material may be needed to give the desired release.

Another method of giving a modified release of bitterness inhibitors is agglomeration with an agglomerating agent which partially coats the bitterness inhibitors. This method includes the step of mixing bitterness inhibitors and an agglomerating agent with a small amount of water or other solvent. The mixture is prepared in such a way as to have individual wet particles in contact with each other so that a partial coating can be applied. After the water or solvent is removed, the mixture is ground and used as a powdered, coated bitterness inhibitor.

Materials that can be used as the agglomerating agent are the same as those used in encapsulation mentioned previously. However, since the coating is only a partial encapsulation, some agglomerating agents are more effective in increasing the bitterness inhibitors' release than others. Some of the better agglomerating agents for delayed release are the organic polymers like acrylic polymers and copolymers, polyvinyl acetate, polyvinylpyrrolidone, waxes, shellac and Zein. Other agglomerating agents are not as effective in giving a delayed release as are the polymers, waxes, shellac and Zein, but can be used to give some delayed release. Other agglomerating agents that give a fast release include, but are not limited to, agar, alginates, a wide range of water soluble cellulose derivatives like ethyl cellulose, methyl cellulose, sodium hydroxymethyl cellulose, hydroxypropylmethyl cellulose, dextrin, gelatin, modified starches, and vegetable gums like guar gum, locust bean gum and carrageenan. Even though the agglomerated bitterness inhibitor is only partially coated, when the quantity of coating is increased compared to the quantity of bitterness inhibitor, the release of bitterness inhibitor can also be modified for mastication. The level of coating used in the agglomerated product is a minimum of about 5%. Preferably, the coating level is a minimum of about 15% and more preferably about 20%. Depending on the agglomerating agent, a higher or lower amount of agent may be needed to give the desired release of bitterness inhibitor.

Bitterness inhibitors may be coated in a two-step process or a multiple step process. Bitterness inhibitors may be encapsulated with any of the materials as described previously and then the encapsulated bitterness inhibitors can be agglomerated as previously described to obtain an encapsulated/agglomerated/bitterness inhibitor product that could be used in chewing gum to give a delayed release of the bitterness inhibitor.

In another embodiment of this invention, bitterness inhibitors may be absorbed onto another component which is porous and become entrapped in the matrix of the porous component. Common materials used for absorbing bitterness inhibitors include, but are not limited to, silicas, silicates, pharmasorb clay, spongelike beads or microbeads, amorphous carbonates and hydroxides, including aluminum and calcium lakes, all of which result in a delayed release of bitterness inhibitors. Other water soluble materials including amorphous sugars such as spray-dried dextrose, sucrose, alditols and vegetable gums and other spray-dried materials result in a faster release of bitterness inhibitors.

Depending on the type of absorbent materials and how it is prepared, the amount of bitterness inhibitors that can be loaded onto the absorbent will vary. Generally materials like polymers or spongelike beads or microbeads, amorphous sugars and alditols and amorphous carbonates and hydroxides absorb about 10% to about 40% of the weight of the absorbent. Other materials like silicas and pharmasorb clays may be able to absorb about 20% to about 80% of the weight of the absorbent.

The general procedure for absorbing a bitterness inhibitor onto the absorbent is as follows. An absorbent like fumed silica powder can be mixed in a powder blender and an aqueous solution of a bitterness inhibitor can be sprayed onto the powder as mixing continues. The aqueous solution can be about 10% to 30% solids, and higher solid levels may be used if temperatures up to 90° C. are used. Generally water is the solvent, but other solvents like alcohol could also be used if approved for use in food. As the powder mixes, the liquid is sprayed onto the powder. Spraying is stopped before the mix becomes damp. The still free-flowing powder is removed from the mixer and dried to remove the water or other solvent, and is then ground to a specific particle size.

After the bitterness inhibitor is absorbed or fixed onto an absorbent, the fixative/inhibitor can be coated by encapsulation. Either full or partial encapsulation may be used, depending on the coating composition used in the process. Full encapsulation may be obtained by coating with a polymer as in spray drying, spray chilling, fluid-bed coating, coacervation, or any other standard technique. A partial encapsulation or coating can be obtained by agglomeration of the fixative inhibitor mixture using any of the materials discussed above.

Another form of encapsulation is by entrapment of an ingredient by fiber extrusion or fiber spinning into a polymer. Polymers that can be used for extrusion are PVAC, hydroxypropyl cellulose, polyethylene and other types of plastic polymers. A process of encapsulation by fiber extrusion is disclosed in U.S. Pat. No. 4,978,537, which is hereby incorporated by reference. The water insoluble polymer may be preblended with the bitterness inhibitor prior to fiber extrusion, or may be added after the polymer is melted. As the extrudate is extruded, it results in small fibers that are cooled and ground. This type of encapsulation/entrapment generally gives a very long, delayed release of an active ingredient.

The four primary methods to obtain a modified release of the bitterness inhibitor are: (1) encapsulation by spray drying, fluid-bed coating, spray chilling and coacervation to give full or partial encapsulation, (2) agglomeration to give partial encapsulation, (3) fixation or absorption which also gives partial encapsulation, and (4) entrapment into an extruded compound. These four methods, combined in any usable manner which physically modifies the release or dissolvability of the bitterness inhibitor, are included in this invention.

A method of modifying the release rate of the bitterness inhibitors from the chewing gum is to add the bitterness inhibitors to the dusting compound of a chewing gum. A rolling or dusting compound may be applied to the surface of chewing gum as it is formed.

This rolling or dusting compound serves to reduce sticking of the chewing gum product to machinery as it is formed and as it is wrapped, and sticking of the product to its wrapper after it is wrapped and is being stored. The rolling compound comprises a bitterness inhibitor powder in combination with mannitol, sorbitol, sucrose, starch, calcium carbonate, talc, other orally acceptable substances or a combination thereof. The rolling compound constitutes from about 0.25% to about 10%, but preferably about 1% to about 3% by weight of the chewing gum composition. The amount of a bitterness inhibitor powder added to the rolling compound is about 0.05% to about 20% of the rolling compound or about 5 ppm to about 2000 ppm of the chewing gum composition. This method of using a bitterness inhibitor powder in the chewing gum allows for a lower usage level of the bitterness inhibitor, gives a bitterness inhibitor a fast release rate, reduces bitterness and reduces or eliminates any possible reaction with gum base, flavor components, or other components, yielding improved shelf stability.

Another method of modifying the release rate of a bitterness inhibitor is to use it in the coating/panning of a pellet chewing gum. Pellet or ball gum is prepared as conventional chewing gum, but formed into pellets that are pillow shaped or into balls. The pellets/balls can then be sugar coated or panned by conventional panning techniques to make a unique sugar coated pellet gum. Bitterness inhibitors may generally be very stable and highly water soluble and can be easily dispersed in a sugar solution prepared for sugar panning. A bitterness inhibitor can also be added as a powder blended with other powders often used in some types of conventional panning procedures. Using a bitterness inhibitor in a coating isolates it from other gum ingredients and modifies its release rate in chewing gum. Levels of a bitterness inhibitor may be about 100 ppm (0.01%) to about 25,000 ppm (2.5%) in the coating and about 50 ppm (0.005%) to about 10,000 ppm (1%) of the weight of the chewing gum product. The weight of the coating may be about 20% to about 50% of the weight of the finished gum product.

Conventional panning procedures generally coat with sucrose, but recent advances in panning have allowed the use of other carbohydrate materials to be used in the place of sucrose. Some of these components include, but are not limited to, dextrose, maltose, palatinose, xylitol, lactitol, hydrogenated isomaltulose and other new alditols or a combination thereof. These materials may be blended with panning modifiers including, but not limited to, gum arabic, maltodextrins, corn syrup, gelatin, cellulose type materials like carboxymethyl cellulose or hydroxymethyl cellulose, starch and modified starches, vegetable gums like alginates, locust bean gum, guar gum, and gum tragacanth, insoluble carbonates like calcium carbonate or magnesium carbonate and talc. Antitack agents may also be added as panning modifiers which allow for the use of a variety of carbohydrates and sugar alcohols in the development of new panned or coated gum products. Flavors may also be added with the sugar coating and with bitterness inhibitors to yield unique product characteristics.

Another type of pan coating would also modify the release rate of bitterness inhibitors from the chewing gum. This technique is referred to as film coating and is more common in pharmaceuticals than in chewing gum, but procedures are similar. A film like shellac, Zein, or cellulose-type material is applied onto a pellet-type product forming a thin film on the surface of the product. The film is applied by mixing the polymer, a plasticizer and a solvent (pigments are optional) and spraying the mixture onto the pellet surface. This is done in conventional type panning equipment, or in more advanced side-vented coating pans. When a solvent like alcohol is used, extra precautions are needed to prevent fires and explosions, and specialized equipment must be used.

Some film polymers can use water as the solvent in film coating. Recent advances in polymer research and in film coating technology eliminates the problem associated with the use of flammable solvents in coating. These advances make it possible to apply aqueous films to a pellet or chewing gum product. Since many bitterness inhibitors are highly water soluble, they may be added to this aqueous film solution and applied with the film to the pellet or chewing gum product. The aqueous film, or even the alcohol solvent film, in which bitterness inhibitors are dispersed may also contain a flavor along with the polymer and plasticizer.

The previously described encapsulated, agglomerated or absorbed bitterness inhibitors may readily be incorporated into a chewing gum composition. The remainder of the chewing gum ingredients are noncritical to the present invention. That is, the coated particles of bitterness inhibitors can be incorporated into conventional chewing gum formulations in a conventional manner. Coated bitterness inhibitors may be used in a sugar chewing gum or a sugarless chewing gum. The coated bitterness inhibitors may be used in either regular chewing gum or bubble gum.

In general, a chewing gum composition typically comprises a water-soluble bulk portion, a water-insoluble chewable gum base portion and typically water-insoluble flavoring agents. The water-soluble portion dissipates with a portion of the flavoring agent over a period of time during chewing. The gum base portion is retained in the mouth throughout the chew.

The insoluble gum base generally comprises elastomers, resins, fats and oils, waxes, softeners and inorganic fillers. Elastomers may include polyisobutylene, isobutylene-isoprene copolymer and styrene butadiene rubber, as well as natural latexes such as chicle. Resins include polyvinylacetate and terpene resins. Fats and oils may also be included in the gum base, including tallow, hydrogenated and partially hydrogenated vegetable oils, and cocoa butter. Commonly employed waxes include paraffin, microcrystalline and natural waxes such as beeswax and carnauba. According to the preferred embodiment of the present invention, the insoluble gum base constitutes between about 5% and about 95% by weight of the gum. More preferably the insoluble gum base comprises between about 10% and about 50% by weight of the gum, and most preferably between about 20% and about 35% by weight of the gum.

The gum base typically also includes a filler component. The filler component may be calcium carbonate, magnesium carbonate, talc, dicalcium phosphate or the like. The filler may constitute between about 5% and about 60% by weight of the gum base. Preferably, the filler comprises about 5% to about 50% by weight of the gum base.

Gum bases typically also contain softeners, including glycerol monostearate and glycerol triacetate. Further, gum bases may also contain optional ingredients such as antioxidants, colors, and emulsifiers. The present invention contemplates employing any commercially acceptable gum base.

The water-soluble portion of the chewing gum may further comprise softeners, sweeteners, flavoring agents and combinations thereof. Softeners are added to the chewing gum in order to optimize the chewability and mouth feel of the gum. Softeners, also known in the art as plasticizers or plasticizing agents, generally constitute between about 0.5% and about 15% by weight of the chewing gum. Softeners contemplated by the present invention include glycerin, lecithin and combinations thereof. Further, aqueous sweetener solutions such as those containing sorbitol, hydrogenated starch hydrolyzates, corn syrup and combinations thereof may be used as softeners and binding agents in gum.

As mentioned above, the coated bitterness inhibitor of the present invention may be used in sugar or sugarless gum formulations. Sugar sweeteners generally include saccharide-containing components commonly known in the chewing gum art which comprise, but are not limited to, sucrose, dextrose, maltose, dextrin, dried invert sugar, fructose, levulose, galactose, corn syrup solids and the like, alone or in any combination. Sugarless sweeteners include components with sweetening characteristics but which are devoid of the commonly known sugars and comprise, but are not limited to, sugar alcohols such as sorbitol, mannitol, xylitol, hydrogenated starch hydrolyzates, maltitol and the like, alone or in any combination.

Depending on the particular bitterness inhibitor release profile and shelf-stability needed, the coated bitterness inhibitor of the present invention can also be used in combination with uncoated high-potency sweeteners or with high-potency sweeteners coated with other materials and by other techniques.

A flavoring agent may also be present in the chewing gum in an amount within the range of from about 0.1% to about 15%, preferably from about 0.5% to about 3%, by weight of the gum. The flavoring agents may comprise essential oils, synthetic flavors, or mixtures thereof including, but not limited to oils derived from plants and fruits such as citrus oils, fruit essences, peppermint oil, spearmint oil, clove oil, oil of wintergreen, anise, and the like. Artificial flavoring components are also contemplated for use in gums of the present invention. Those skilled in the art will recognize that natural and artificial flavoring agents may be combined in any sensorally acceptable blend. All such flavors and flavor blends are contemplated by the present invention.

Optional ingredients such as colors, emulsifiers and pharmaceutical agents may be added to the chewing gum.

In general, chewing gum is manufactured by sequentially adding the various chewing gum ingredients to a commercially available mixer known in the art. After the ingredients have been thoroughly mixed, the gum mass is discharged from the mixer and shaped into the desired form such as by rolling into sheets and cutting into sticks, extruding into chunks or casting into pellets.

Generally, the ingredients are mixed by first melting the gum base and adding it to the running mixer. The base may also be melted in the mixer itself. Color or emulsifiers may also be added at this time. A softener such as glycerin may also be added at this time, along with syrup and a portion of the bulking agent. Further portions of the bulking agent may then be added to the mixer. A flavoring agent is typically added with the final portion of the bulking agent. The coated bitterness inhibitor of the present invention is preferably added after the final portion of bulking agent and flavor have been added.

The entire mixing procedure typically takes from five to fifteen minutes, but longer mixing times may sometimes be required. Those skilled in the art will recognize that many variations of the above described procedure may be followed.

EXAMPLES

The following examples of the invention and comparative examples are provided by way of explanation and illustration.

The formulas listed in Table 1 comprise various sugar formulas in which the bitterness inhibitor sodium gluconate can be added to gum after it is dissolved in various aqueous type solvents.

TABLE 1

| | (Wt. %) | | | | | |
|---|---|---|---|---|---|---|
| | Example 1 | Example 2 | Example 3 | Example 4 | Example 5 | Example 6 |
| Sugar | 61.9 | 60.4 | 60.8 | 60.8 | 60.8 | 58.3 |
| Gum Base | 19.2 | 19.2 | 19.2 | 19.2 | 19.2 | 19.2 |
| Glycerin | 1.4 | 1.4 | 0.0 | 0.0 | 0.0 | 1.4 |
| Corn Syrup | 15.9 | 15.9 | 12.9 | 12.9 | 12.9 | — |
| Lecithin | 0.2 | 0.2 | 0.2 | 0.2 | 0.2 | 0.2 |
| Peppermint Flavor | 0.9 | 0.9 | 0.9 | 0.9 | 0.9 | 0.9 |
| Liquid/Sodium Gluconate blend | 0.5 | 2.0 | 6.0 | 6.0 | 6.0 | 20.0 |

Example 1 and 2

Sodium gluconate powder can be added directly to the gum.

Example 3

A 20.0 gram portion of sodium gluconate can be dissolved in 80.0 grams of hot water, making a 20.0% solution, and added to gum.

Example 4

A 5.0 gram portion of sodium gluconate can be dissolved in 95.0 grams of hot propylene glycol, making a 5.0% solution, and added to gum.

Example 5

A 5.0 gram portion of sodium gluconate can be dissolved in 95.0 grams of hot glycerin, making a 5.0% solution, and added to gum.

Example 6

A 2.5 gram portion of sodium gluconate can be dissolved in hot corn syrup, making a 2.5% solution, and added to gum.

In the next examples of a sugar gum formulation, sodium gluconate can be dissolved in hot water and emulsifiers can be added to the aqueous solution. Example solutions can be prepared by dissolving 10 grams of sodium gluconate in 90 grams hot water and adding 5 grams of emulsifiers of various hydrophilic-lipophilic balance(HLB) values to the solution. The mixtures can then be used in the following formulas.

TABLE 2

| | (WT. %) | | | | | |
|---|---|---|---|---|---|---|
| | Example 7 | Example 8 | Example 9 | Example 10 | Example 11 | Example 12 |
| Sugar | 50.7 | 50.7 | 50.7 | 50.7 | 50.7 | 50.7 |
| Base | 19.2 | 19.2 | 19.2 | 19.2 | 19.2 | 19.2 |
| Corn Syrup | 12.9 | 12.9 | 12.9 | 12.9 | 12.9 | 12.9 |
| Glycerin | 1.4 | 1.4 | 1.4 | 1.4 | 1.4 | 1.4 |
| Dextrose Monohydrate | 9.9 | 9.9 | 9.9 | 9.9 | 9.9 | 9.9 |
| Peppermint Flavor | 0.9 | 0.9 | 0.9 | 0.9 | 0.9 | 0.9 |
| Sodium Gluconate/ Emulsifier Water Mixture | None | HLB = 2 | HLB = 4 | HLB = 6 | HLB = 9 | HLB = 12 |
| | 5.0 | 5.0 | 5.0 | 5.0 | 5.0 | 5.0 |

Examples 13–18

The same as the formulations made in Examples 7–12, respectively, except that the flavor can be mixed together with the aqueous sodium gluconate solution and emulsified before adding the mixture to the gum batch.

Sodium gluconate can also be blended into various base ingredients. A typical base formula is as follows:

| | Wt. % |
|---|---|
| Polyvinyl acetate | 27 |
| Synthetic rubber | 13 |
| Paraffin Wax | 13 |
| Fat | 3 |
| Glycerol Monostearate | 5 |
| Terpene Resin | 27 |
| Calcium Carbonate Filler | 12 |
| | 100% |

The individual base components can be softened prior to their addition in the base manufacturing process. To the presoftened base component, sodium gluconate can be added and mixed, and then the presoftened base/sodium gluconate blend can be added to make the finished base. In the following examples, sodium gluconate can be mixed first with one of the base ingredients, and the mixed ingredient can then be used in making a base. The ingredients blended with sodium gluconate can then be used at the levels indicated in the typical base formula above.

Example 19

The terpene resin used to make the base is 98% polyterpene resin and 2% sodium gluconate.

Example 20

The polyvinyl acetate used to make the base is 98% low M.W. polyvinyl acetate and 2% sodium gluconate.

Example 21

The paraffin wax used to make the base is 96% paraffin wax and 4% sodium gluconate.

Sodium gluconate may also be added to an otherwise complete gum base.

Example 22

0.5% sodium gluconate can be mixed with 99.5% of a gum base having the above listed typical formula. The sodium gluconate can be added near the end of the process after all the other ingredients are added.

The samples of finished base made with sodium gluconate added to different base components can then be evaluated in a sugar-type chewing gum formulated as follows:

TABLE 3

| (Wt. %) | |
|---|---|
| (For examples 19, 20, 21, and 22) | |
| Sugar | 55.2 |
| Base | 19.2 |
| Corn Syrup | 13.4 |
| Glycerine | 1.4 |
| Dextrose Monohydrate | 9.9 |
| Peppermint Flavor | 0.9 |
| | 100% |

The theoretical level of sodium gluconate in the finished gum is 0.1%.

Using the following formulation of a sugar or sugar-free gum, a variety of encapsulated sodium gluconate samples can be evaluated:

TABLE 4

| | (Wt. %) | |
|---|---|---|
| | Sugar Free | Sugar |
| Sorbitol | 48.8 | — |
| Sugar | — | 54.7 |
| Mannitol | 8.0 | — |
| Gum Base | 25.5 | 20.0 |
| Glycerin | 8.5 | 1.4 |
| Corn Syrup | — | 12.0 |
| Lycasin brand Hydrogenated Starch Hydrolyzates | 6.8 | — |
| Dextrose Monohydrate | — | 10.0 |
| Peppermint Flavor | 1.4 | 0.9 |
| Active Sodium Gluconate | 1.0% | 1.0% |

For spray drying, the solids level of an aqueous or alcoholic solution can be about 5–30%, but preferred levels are indicated in the examples listed.

Example 23

An 80% shellac, 20% active sodium gluconate powder mixture is obtained by spray drying an alcohol/shellac/sodium gluconate solution at total solids of 20%.

Example 24

A 50% shellac, 50% active sodium gluconate powder mixture is obtained by spray drying an appropriate ratio of alcohol/shellac/sodium gluconate solution at 20% solids.

Example 25

A 70% Zein, 30% active sodium gluconate powder mixture is obtained by spray drying an alcohol/Zein/sodium gluconate solution at 10% solids.

Example 26

A 40% shellac, 60% active sodium gluconate powder mixture is obtained by fluid-bed coating sodium gluconate with an alcohol/shellac solution at 30% solids.

Example 27

A 60% shellac, 40% active sodium gluconate powder mixture is obtained by fluid-bed coating sodium gluconate with an alcohol/shellac solution at 30% solids.

Example 28

A 40% Zein, 60% active sodium gluconate powder mixture is obtained by fluid-bed coating sodium gluconate with an alcohol/Zein solution at 25% solids.

Example 29

An 85% wax, 15% active sodium gluconate powder mixture is obtained by spray chilling a mixture of molten wax and sodium gluconate.

Example 30

A 70% wax, 30% active sodium gluconate powder mixture is obtained by spray chilling a mixture of molten wax and sodium gluconate.

Example 31

A 70% Zein, 30% active sodium gluconate powder mixture is obtained by spray drying a hot aqueous mixture of sodium gluconate and Zein dispersed in an aqueous, high-pH (pH of 11.6–12.0) media at 10% solids.

Example 32

A 20% Zein, 80% active sodium gluconate powder mixture is obtained by fluid-bed coating sodium gluconate with an aqueous, high-pH (pH=11.6–12.0) Zein dispersion of 10% solids.

Example 33

A 20% Zein, 20% shellac, 60% active sodium gluconate powder mixture is obtained by spray drying an alcohol/shellac/sodium gluconate mixture and then fluid-bed coating the spray dried product for a second coating of alcohol and Zein.

Examples 23 to 33 would all give nearly complete encapsulation and would delay the release of sodium gluconate when used in the sugar or sugarless gum formulations in Table 4. The higher levels of coating would give a longer delayed release of sodium gluconate than the lower levels of coating.

Other polymers that are more water soluble and used in coating would have a slower release of the sodium gluconate.

Example 34

An 80% gelatin, 20% active sodium gluconate powder mixture is obtained by spray drying a hot gelatin/sodium gluconate solution at 20% solids.

Example 35

A 30% hydroxypropylmethyl cellulose (HPMC), 70% sodium gluconate powder mixture is obtained by fluid-bed coating sodium gluconate with an aqueous solution of HPMC at 10% solids.

Example 36

A 50% maltodextrin, 50% active sodium gluconate powder mixture is obtained by spray drying a hot aqueous solution of sodium gluconate and maltodextrin at 30% solids.

Example 37

A 40% gum arabic, 60% active sodium gluconate powder mixture is obtained by fluid-bed coating sodium gluconate with an aqueous solution of gum arabic at 30% solids.

The coated sodium gluconate from Examples 34 and 35, when used in the chewing gum formulas in Table 4, would give a slightly slow release of sodium gluconate. The product coated with maltodextrin and gum arabic in Examples 36 and 37, when used in the gum formulas in Table 4, would show a fast release of sodium gluconate in chewing gum compared to sodium gluconate added directly.

Sodium gluconate could also be used in gum as an agglomerated sodium gluconate to give fast or delayed sodium gluconate release. Agglomerated sodium gluconate can be prepared as in the following examples:

Example 38

A 15% hydroxypropylmethyl cellulose (HPMC), 85% active sodium gluconate powder mixture is prepared by agglomerating sodium gluconate and HPMC blended together, with water being added, and the resulting product being dried and ground.

Example 39

A 15% gelatin, 85% active sodium gluconate powder mixture is made by agglomerating sodium gluconate and gelatin blended together, with water being added, and the resulting product being dried and ground.

Example 40

A 10% Zein, 90% active sodium gluconate powder mixture is made by agglomerating sodium gluconate with an alcohol solution containing 25% Zein, and drying and grinding the resulting product.

Example 41

A 15% shellac, 85% active sodium gluconate powder mixture is made by agglomerating sodium gluconate with an alcohol solution containing 25% shellac, and drying and grinding the resulting product.

Example 42

A 20% HPMC, 80% active sodium gluconate powder mixture is obtained by agglomerating an HPMC and sodium gluconate mixture blended together, with water being added, and the resulting product being dried and ground.

Example 43

A 20% Zein, 80% active sodium gluconate powder mixture is obtained by agglomerating sodium gluconate and Zein dissolved in high-pH water (11.6–12.0) at 15% solids, with the resulting product being dried and ground.

Example 44

A 20% wax, 80% active sodium gluconate powder mixture is obtained by agglomerating sodium gluconate and molten wax, and cooling and grinding the resulting product.

Example 45

A 15% maltodextrin, 85% active sodium gluconate powder mixture is obtained by agglomerating a blend of sodium gluconate and maltodextrin, then adding water, drying and grinding.

All of the above mixtures can be added to any of the following types of chewing gum formulas:

TABLE 5

| | | (Wt. %) | | |
| --- | --- | --- | --- | --- |
| | Sugar | Sugarless With Water | Sugarless With Lycasin | Sugarless No Water |
| | Sugar With Sorbitol | | | |
| Gum Base | 19.2 | 19.2 | 25.5 | 25.5 | 25.5 |
| Sugar | 55.0 | 53.0 | — | — | — |
| Sorbitol | — | 2.0 | 52.8 | 48.5 | 51.3 |
| Mannitol | — | — | 8.0 | 8.0 | 12.0 |
| Corn Syrup | 13.1 | 13.1 | — | — | — |
| Lycasin/Sorbitol liquid | — | — | 9.5$^{(a)}$ | 6.8$^{(b)}$ | — |
| Glycerin | 1.4 | 1.4 | 1.5 | 8.5 | 8.5 |
| Lecithin | — | — | 0.2 | 0.2 | 0.2 |
| Dextrose Monohydrate | 9.9 | 9.9 | — | — | — |
| Flavor | 0.9 | 0.9 | 1.5 | 1.5 | 1.5 |
| Level of Active Sodium Gluconate | 0.5 | 0.5 | 1.0 | 1.0 | 1.0 |

$^{(a)}$liquid sorbitol (70% sorbitol, 30% water)
$^{(b)}$hydrogenated starch hydrolyzate syrup Partially coated or fully coated sodium gluconate can also be used in sugar type gum formulations containing other sugars, such as in the following formulations A–G:

TABLE 6

| | (Wt. %) | | | | | | |
| --- | --- | --- | --- | --- | --- | --- | --- |
| | A | B | C | D | E | F | G |
| Gum Base | 19.2 | 19.2 | 19.2 | 19.2 | 19.2 | 19.2 | 19.2 |
| Sugar | 58.5 | 49.5 | 48.5 | 48.5 | 49.5 | 51.5 | 51.5 |
| Glycerin | 1.4 | 1.4 | 1.4 | 1.4 | 1.4 | 1.4 | 1.4 |
| Corn Syrup | 19.0 | 23.0 | 19.0 | 19.0 | 23.0 | 16.0 | 16.0 |
| Dextrose | — | — | 5.0 | — | — | — | — |
| Lactose | — | — | — | — | 5.0 | — | — |
| Fructose | — | — | 5.0 | — | — | — | — |
| Invert Sugar | — | — | — | 10.0 | — | — | — |
| Maltose | — | — | — | — | — | 10.0 | — |
| Palatinose | — | — | — | — | — | — | 10.0 |
| Corn Syrup Solids | — | 5.0 | — | — | — | — | — |
| Peppermint Flavor | 0.9 | 0.9 | 0.9 | 0.9 | 0.9 | 0.9 | 0.9 |
| Level of Active Sodium Gluconate | 1.0 | 1.0 | 1.0 | 1.0 | 1.0 | 1.0 | 1.0 |

These formulations may also contain sugar alcohols such as sorbitol, mannitol, xylitol, lactitol, maltitol, hydrogenated isomaltulose, and Lycasin or combinations thereof. Sugarless type gum formulations with partially coated or fully coated sodium gluconate can also be made using various sugar alcohols, such as the following formulations H–P:

TABLE 7

| | (Wt. %) | | | | | | | | |
| --- | --- | --- | --- | --- | --- | --- | --- | --- | --- |
| | H | I | J | K | L | M | N | O | P |
| Base | 25.5 | 25.5 | 25.5 | 25.5 | 25.5 | 25.5 | 25.5 | 25.5 | 25.5 |
| Sorbitol | 53.0 | 46.0 | 41.0 | 41.0 | 41.0 | 41.0 | 36.0 | 37.0 | 46.0 |
| Sorbitol Liquid/Lycasin | 17.0 | 14.0 | 6.0 | — | 5.0 | — | — | 6.0$^{(a)}$ | 18.0$^{(a)}$ |
| Mannitol | — | 10.0 | 8.0 | 8.0 | 8.0 | 8.0 | 8.0 | 8.0 | 8.0 |
| Maltitol | — | — | — | 5.0 | — | — | 5.0 | — | — |
| Xylitol | — | — | 15.0 | 10.0 | — | — | 5.0 | 15.0 | — |
| Lactitol | — | — | — | — | 10.0 | — | — | — | — |
| Hydrogenated Isomaltulose | — | — | — | — | — | 15.0 | 10.0 | — | — |
| Glycerin | 2.0 | 2.0 | 2.0 | 8.0 | 8.0 | 8.0 | 8.0 | 6.0 | — |
| Flavor | 1.5 | 1.5 | 1.5 | 1.5 | 1.5 | 1.5 | 1.5 | 1.5 | 1.5 |
| Level of Active Sodium Gluconate | 1.0 | 1.0 | 1.0 | 1.0 | 1.0 | 1.0 | 1.0 | 1.0 | 1.0 |

$^{(a)}$Lycasin, all others use sorbitol liquid

If each of the examples of agglomerated material (38–45) were evaluated in the formulations shown in Table 5, most samples would give sodium gluconate a delayed release. Samples using Zein, wax, and shellac would yield the slowest release rate, whereas samples with HPMC and gelatin would yield the next slowest release. Maltodextrin would give a release compared to sodium gluconate added directly to the gum.

All of these formulations in Table 6 and Table 7 which use the agglomerated sodium gluconate as described in the examples (38–45) and in the previous encapsulated examples (23–35) would be expected to give a delayed release of sodium gluconate compared to a product made by adding sodium gluconate directly to gum as a powder.

Multiple step agglomeration/encapsulation procedures can also be used in making release-modified sodium gluconate for use in the formulations in Tables 5, 6 and 7. Examples of multiple step treatments are here described:

Example 46

Sodium gluconate is spray dried with maltodextrin at 30% solids to prepare a powder. This powder is then agglomerated with a hydroxypropylmethyl cellulose (HPMC) in a ratio of 85/15 powder/HPMC, wetted with water and dried. After grinding the resulting powder will contain about 68% active sodium gluconate, 17% maltodextrin and 15% HPMC.

Example 47

Sodium gluconate is agglomerated with HPMC in a ratio of 85/15 sodium gluconate/HPMC. After drying and grinding, the resulting powder is fluid-bed coated with an alcohol/shellac solution at about 25% solids to give a final product containing about 60% active sodium gluconate, 10% HPMC, and about 30% shellac.

Example 48

Sodium gluconate is agglomerated with HPMC in a ratio of 85/15 sodium gluconate/HPMC. After drying and grinding, the resulting powder is agglomerated with a 15% solids, high-pH, aqueous solution of Zein to give a final product containing about 60% active sodium gluconate, 10% HPMC, and 30% Zein.

Example 49

Sodium gluconate is spray dried with a 25% solution of gelatin. The spray dried product is then agglomerated with a 15% solids, high-pH, aqueous solution of Zein. The final product will contain about 50% active sodium gluconate, 20% gelatin, and 30% Zein.

Example 50

Sodium gluconate is agglomerated with molten wax in a ratio of 85/15 sodium gluconate/wax. When the mixture cools and is ground, it is fluid-bed coated with a 25% Zein-75% alcohol solution, giving a final product containing 60% active sodium gluconate, 10% wax and 30% Zein.

These examples 46–50, when used in any of the formulations noted in Tables 5, 6, and 7 above, give sodium gluconate a delayed release. These multiple step procedures can actually give more delayed release than the single step processes. Multiple step processes of more than two steps may give even longer delayed release times, but may generally become less cost effective and less efficient. Preferably, spray drying can be the first step with additional steps of fluid-bed coating, spray chilling and agglomeration being part of the latter steps.

For absorption type examples, the delayed release rate of sodium gluconate is dependent on the type of absorbing material. Most materials like silicas, silicates, cellulose, carbonates, and hydroxides would be expected to give a more delayed release than amorphous sugar and sugar alcohols. Some examples:

Example 51

A 20% solution of sodium gluconate is sprayed onto a precipitated silica to absorb the sodium gluconate. The mixture is dried and ground and the final product is about 50% active sodium gluconate.

Example 52

A 20% solution of sodium gluconate is sprayed onto a pharmasorb clay. The mixture is dried and ground and gives a final product of about 80% clay and 20% active sodium gluconate.

Example 53

A 20% solution of sodium gluconate is sprayed onto a microcrystalline cellulose powder. The mixture is dried and ground and gives a product that is about 70% microcrystalline cellulose and 30% active sodium gluconate.

Example 54

A 20% solution of sodium gluconate is sprayed onto a high absorption starch. The mixture is dried and ground and gives a product that is about 80% starch and 20% active sodium gluconate.

Example 55

A 20% solution of sodium gluconate is sprayed onto a calcium carbonate powder. The mixture is dried and ground and gives a product of about 90% calcium carbonate and 10% active sodium gluconate.

Example 56

A 20% solution of sodium gluconate is sprayed onto a highly absorptive dextrose material. The mixture is dried and ground and gives a product of about 80% dextrose and 20% active sodium gluconate.

Example 57

A 20% solution of sodium gluconate is sprayed onto a sorbitol powder to absorb the material. The mixture is dried and ground and gives a product of about 90% sorbitol and 10% active sodium gluconate.

The samples prepared in examples 51–57 can be used in gum formulations as noted in Tables 5, 6, and 7. Those preparations which have sodium gluconate absorbed onto a material that is not water soluble are expected to give a delayed release and those that are water soluble are expected to give fast release.

Another modification or absorption technique is to dry the sodium gluconate together with a sugar or sugar alcohol, or resolidify the sodium gluconate with sugar or sugar alcohol when mixed together in a molten state.

Example 58

Sodium gluconate is added to molten sorbitol in a ratio of 90 parts sorbitol to 10 parts sodium gluconate. After mixing, the blend is cooled and ground.

Example 59

Sodium gluconate is added to molten dextrose in a ratio of 90 parts dextrose to 10 parts sodium gluconate. After mixing, the blend is cooled and ground.

Example 60

4% sodium gluconate is dissolved in 96% high fructose corn syrup. The mixture is evaporated to a low moisture and ground.

The product of examples 58–60 may be added to the gum formulations shown in Tables 5, 6 and 7.

Many of the examples listed are single step processes. However, more delayed release of the sodium gluconate may be obtained by combining the various processes of encapsulation, agglomeration, absorption, and entrapment. Any of the preparations made in examples 51–60 can be further treated in fluid-bed coating, spray chilling, or coacervation processes to encapsulate the product, and can be agglomerated with various materials and procedures in a variety of multiple step processes.

The sodium gluconate can also be used with a variety of high-intensity sweeteners and blended together before encapsulation, agglomeration, absorption, and entrapment. This can reduce bitterness associated with some stimulants such as caffeine. Some examples are:

Example 61

Sodium gluconate and aspartame are blended together in a 2/1 ratio as a powder. This mixture is then spray chilled with wax in a ratio of 60/40 mixture/wax to obtain a powder containing 40% sodium gluconate, 20% aspartame, and 40% wax.

Example 62

Sodium gluconate and thaumatin in a 4/1 ratio are dissolved in water with a 10% solution of gelatin and spray dried. This spray dried powder is then agglomerated with a high-pH aqueous 15% Zein solution. The mixture is dried and ground and gives a product containing 40% sodium gluconate, 10% thaumatin, 35% gelatin, and 15% Zein.

Example 63

Sodium gluconate and alitame in a 7/1 ratio are prepared in a 20% solution. This solution is sprayed onto a high absorption silica powder. The mixture is dried, ground and fluid-bed coated with an alcohol/shellac mixture, giving a product that contains 35% sodium gluconate, 5% alitame, 40% silica, and 20% shellac.

Example 64

Sodium gluconate and sodium cyclamate in a 1/1 ratio are blended together as a powder and then agglomerated with water and hydroxypropylmethyl cellulose (HPMC). This blend is dried, ground and agglomerated further with a high-pH, aqueous 15% solution of Zein to obtain a product containing 34% sodium cyclamate, 34% sodium gluconate, 12% HPMC and 20% Zein.

Example 65

Sodium gluconate and glycyrrhizin in a 1/1 ratio are blended together as a powder and fluid-bed coated with a solution of 25% shellac in alcohol. The coated product is agglomerated further with water and hydroxypropylmethyl cellulose (HPMC) to obtain a product containing 30% sodium gluconate, 30% glycyrrhizin, 25% shellac, and 15% HPMC.

Example 66

Sodium gluconate and sodium saccharin in a ratio of 1/1 are blended together as a powder and fluid bed coated with a solution of 25% shellac in alcohol. The coated product is agglomerated further with water and hydroxypropylmethyl cellulose (HPMC) to obtain a product containing 30% sodium gluconate, 30% sodium saccharin, 25%; shellac, and 15% HPMC.

If the blends of sodium gluconate and other high-intensity sweeteners of examples 61–66 are tested in gum formulations such as those noted in Tables 4, 5, 6 and 7, a significant delayed release of the sweetener and bitterness inhibitor would be expected. This delayed release would improve the quality of flavor. The following are examples of fiber extruded PVAC/sodium gluconate blends to give a delayed release of sodium gluconate and give reduced bitterness:

Example 67

Medium molecular weight PVAC and sodium gluconate at a ratio of 3/1 are blended together as a powder and extruded. The fibers are cooled and ground to give a product containing 75% PVAC and 25% sodium gluconate.

Example 68

Medium molecular weight PVAC, sodium gluconate and aspartame at a ratio of 12/4/1 are blended together as a powder and extruded, the resulting fibers are ground and give a product containing 70% PVAC, 24% sodium gluconate and 6% aspartame.

Example 69

Medium molecular weight PVAC, caffeine, aspartame, and sodium gluconate at a ratio of 16/4/4/1 are blended together as a powder and extruded. The fibers are ground and gives a product containing 64% PVAC, 16% caffeine, 16% sodium gluconate, and 4% aspartame.

Sodium gluconate bitterness inhibitor can be mixed with caffeine before being encapsulated or entrapped. This bitterness inhibitor or other bitterness inhibitors can be added to caffeine to reduce bitterness with fast release or delayed release of both caffeine and sodium gluconate.

Example 70

A 20% hot aqueous solution of maltodextrin is mixed with a 40% hot solution of sodium gluconate. Two liters of this mixture is combined with 100 grams of caffeine, dispersed and spray dried. A final product containing 50% maltodextrin, 33% sodium gluconate and 17% caffeine is obtained.

Example 71

A 2400 ml quantity of a 25% hot aqueous solution of maltodextrin is mixed with 50 grams of aspartame to form a suspension. To this is added a hot aqueous solution of 400 grams of sodium gluconate, 200 grams of caffeine, 1200 grams of hot water. This mixture is spray dried to obtain a powder containing 48% maltodextrin, 32% sodium gluconate, 16% caffeine and 4% aspartame.

Example 72

To a 2400 gram quantity of a 25% hot solution of maltodextrin, 200 grams of citric acid and 50 grams of aspartame are added and suspended. To this mixture is added a hot aqueous solution of 400 grams of sodium gluconate, 200 grams of caffeine and 1200 grams of hot water. This mixture is spray dried to obtain a powder containing 41% maltodextrin, 28% sodium gluconate, 14% caffeine, 14% citric acid and 3% aspartame.

The above examples are made to obtain not only a fast release of caffeine in chewing gum, based on maltodextrin encapsulation, but also to obtain fast release of a sweetener and bitterness inhibitors to counteract bitter effects of caffeine.

It should be appreciated that the methods and compositions of the present invention are capable of being incorporated in the form of a variety of embodiments, only a few of which have been illustrated and described above. The invention may be embodied in other forms without departing from its spirit or essential characteristics. It will be appreciated that the addition of some other ingredients, process steps, materials or components not specifically included will have an adverse impact on the present invention. The best mode of the invention may therefore exclude ingredients, process steps, materials or components other than those listed above for inclusion or use in the invention. However, the described embodiments are to be considered in all respects only as illustrative and not restrictive, and the scope of the invention is, therefore, indicated by the appended claims rather than by the foregoing description. All changes which come within the meaning and range of equivalency of the claims are to be embraced within their scope.

We claim:

1. A method of producing a chewing gum product containing a physically-modified bitterness inhibitor in order to control the release rate of the bitterness inhibitor comprising the steps of:
   a) mixing a quantity of a bitterness inhibitor with a modifying agent, the bitterness inhibitor being other than a high-intensity sweetener; and
   b) adding a quantity of the mixture and caffeine to a chewing gum formulation to provide a bitterness inhibitor level in the chewing gum formulation of from about 0.05% to about 8.0%.

2. The method of claim 1 wherein said modifying agent is an encapsulating agent.

3. The method of claim 2 wherein the bitterness inhibitor is fluid-bed coated with a solution of encapsulating agent and solvent in order to decrease the rate of release of the bitterness inhibitor in the chewing gum.

4. The method of claim 3 wherein the solvent is selected from the group consisting of alcohol and water.

5. The method of claim 3 wherein the encapsulating material is selected from the group consisting of shellac and Zein.

6. The method of claim 3 wherein a high-potency sweetener selected from the group consisting of aspartame, alitame, salts of acesulfame, cyclamate and its salts, saccharin and its salts, thaumatin, monellin, dihydrochalcones and combinations thereof is mixed in the mixture in combination with the bitterness inhibitor.

7. The method of claim 3 wherein the bitterness inhibitor is selected from the group consisting of ferulic acid, sodium gluconate, sodium ferulate, sodium ascorbate, sodium acetate, sodium glycinate and calcium glycerolphosphate.

8. The method of claim 2 wherein the bitterness inhibitor is encapsulated by coacervation in order to decrease the rate of release of bitterness inhibitor in chewing gum.

9. The method of claim 2 wherein the bitterness inhibitor is mixed with a molten encapsulating agent and the bitterness inhibitor is encapsulated by spray chilling in order to decrease the rate of release of the bitterness inhibitor in the chewing gum.

10. The method of claim 9 wherein the encapsulating agent comprises wax.

11. The method of claim 2 wherein the bitterness inhibitor is mixed with a polymer as the encapsulating agent and the resulting mixture is extruded into fibers in such a way as to encapsulate the bitterness inhibitor in order to decrease the rate of release of the bitterness inhibitor in the chewing gum.

12. The method of claim 11 wherein the polymer is selected from the group consisting of PVAC, hydroxypropyl cellulose, polyethylene and plastic polymers.

13. The method of claim 1 wherein the bitterness inhibitor and encapsulating agent are also mixed with a solvent and the resulting mixture is dried prior to being added to the chewing gum.

14. The method of claim 13 wherein the encapsulating material is selected from the group consisting of maltodextrin and gum arabic.

15. The method of claim 13 wherein the mixture is spray dried and the solvent is selected from the group consisting of alcohol and water.

16. The method of claim 1 wherein a high-potency sweetener selected from the group consisting of aspartame, alitame, salts of acesulfame, cyclamate and its salts, saccharine and its salts, thaumatin, monellin, dihydrochalcones and combinations thereof is mixed in the mixture in combination with the bitterness inhibitor.

17. The method of claim 1 wherein the bitterness inhibitor is selected from the group consisting of ferulic acid, sodium gluconate, sodium ferulate, sodium ascorbate, sodium acetate, sodium glycinate and calcium glycerolphosphate.

18. The method of claim 1 wherein the bitterness inhibitor is mixed with an absorbent as the modifying agent.

19. The method of claim 1 wherein the bitterness inhibitor comprises sodium gluconate.

20. A chewing gum product made according to the method of claim 1.

21. The method of claim 1 wherein the bitterness inhibitor is selected from the group consisting of glucono delta lactone; sodium gluconate; potassium gluconate; calcium chloride; neodiosmin; cyclotetradecenones: sclareolide; natural soy flavor; N-sulfomethyl-N-arylureas; sodium, potassium and ammonium salts of ferulic acid and caffeic acid; 2,4-dihydroxy benzoic acid; ferulic acid; sodium ascorbate; sodium acetate; sodium glycinate; calcium glycerolphosphate; sodium glycerolphosphate and mixtures thereof.

22. A method of producing a chewing gum containing a physically-modified bitterness inhibitor in order to control the release rate of the bitterness inhibitor comprising the steps of:
   a) mixing a quantity of the bitterness inhibitor with an agglomerating agent and a solvent to partially coat the bitterness inhibitor, the bitterness inhibitor being other than a high-intensity sweetener;
   b) removing the solvent from the mixture of bitterness inhibitor and agglomerating agent to form a dried material; and
   c) adding a quantity of the dried material and caffeine to a chewing gum formulation to provide a bitterness Inhibitor level in gum of from about 0.05% to about 8.0%.

23. The method of claim 22 wherein the level of coating on the agglomerated bitterness inhibitor is at least about 5%.

24. The method of claim 22 wherein the level of coating on the agglomerated bitterness inhibitor is at least about 15%.

25. The method of claim 22 wherein the level of coating on the agglomerated bitterness inhibitor is at least about 20%.

26. The method of claim 22 wherein the dried material is ground to a powder prior to adding the dried material to the chewing gum.

27. The method of claim 22 wherein the bitterness inhibitor is selected from the group consisting of glucono delta lactone: sodium gluconate; potassium gluconate; calcium chloride; neodiosmin; cyclotetradecenones: sclareolide; natural soy flavor; N-sulfomethyl-N-arylureas; sodium, potassium and ammonium salts of ferulic acid and caffeic acid; 2,4-dihydroxy benzoic acid; ferulic acid; sodium ascorbate; sodium acetate; sodium glycinate; calcium glycerolphosphate; sodium glycerolphosphate and mixtures thereof.

28. A method of producing a chewing gum product containing a bitterness inhibitor and caffeine comprising the steps of providing a chewing gum product and adding caffeine and a bitterness inhibitor to said product wherein the bitterness inhibitor is other than a high intensity sweetener and is added as a part of a rolling compound applied on the chewing gum product.

29. The method of claim 28 wherein the bitterness inhibitor is selected from the group consisting of glucono delta lactone; sodium gluconate; potassium gluconate; calcium chloride; neodiosmin; cyclotetradecenones: sclareolide; natural soy flavor; N-sulfomethyl-N-arylureas; sodium, potassium and ammonium salts of ferulic acid and caffeic acid; 2,4-dihydroxy benzoic acid; ferulic acid; sodium ascorbate; sodium acetate; sodium glycinate; calcium glycerolphosphate; sodium glycerolphosphate and mixtures thereof.

30. A method of producing a chewing gum product containing a bitterness inhibitor and caffeine comprising the steps of providing a chewing gum pellet and adding a bitterness inhibitor wherein the bitterness inhibitor is other than a high-intensity sweetener and is added as a part of a coating on the chewing gum pellet and wherein the caffeine is added as part of said pellet, said coating or both.

31. The method of claim 30 wherein the bitterness inhibitor is selected from the group consisting of glucono delta lactone; sodium gluconate; potassium gluconate; calcium chloride; neodiosmin; cyclotetradecenones; sclareolide; natural soy flavor; N-sulfomethyl-N-arylureas; sodium, potassium and ammonium salts of ferulic acid and caffeic acid; 2,4-dihydroxy benzoic acid, ferulic acid; sodium ascorbate: sodium acetate; sodium glycinate; calcium glycerolphosphate; sodium glycerolphosphate and mixtures thereof.

\* \* \* \* \*